United States Patent
Fields et al.

(10) Patent No.: US 6,972,561 B2
(45) Date of Patent: Dec. 6, 2005

(54) INTERNAL EDDY CURRENT INSPECTION

(75) Inventors: Michael Wayne Fields, Loveland, OH (US); Michael Leonard Dziech, Cincinnati, OH (US); Jon Russel Dierdorf, Okeana, OH (US); Anthony William Mellors, West Chester, OH (US); James Michael Johnson, Kennewick, WA (US)

(73) Assignee: General Electric Company, Schenectady, NY (US)

( * ) Notice: Subject to any disclaimer, the term of this patent is extended or adjusted under 35 U.S.C. 154(b) by 6 days.

(21) Appl. No.: 10/376,517

(22) Filed: Feb. 28, 2003

(65) Prior Publication Data
US 2004/0169510 A1    Sep. 2, 2004

(51) Int. Cl.[7] ............................................. G01N 27/72
(52) U.S. Cl. ........................ 324/219; 324/228; 324/261
(58) Field of Search ............................... 324/219, 228, 324/238–242, 260–262; 33/542–544.1; 73/618–625, 73/660–661, 866.5

(56) References Cited

U.S. PATENT DOCUMENTS

| | | | |
|---|---|---|---|
| 3,279,079 A * | 10/1966 | Schiler | 33/556 |
| 3,833,852 A * | 9/1974 | Schoch | 324/71.1 |
| 4,188,167 A | 2/1980 | Abell | |
| 4,644,274 A * | 2/1987 | Casarcia | 324/262 |
| 4,891,986 A | 1/1990 | Teagle | |
| 5,174,165 A * | 12/1992 | Pirl | 73/866.5 |
| 5,207,005 A * | 5/1993 | Amos et al. | 33/501.04 |
| 5,345,514 A | 9/1994 | Mahdavieh et al. | |
| 5,402,981 A * | 4/1995 | McMurtry | 248/638 |
| 5,442,286 A | 8/1995 | Sutton et al. | |
| 5,479,834 A | 1/1996 | Sanagawa et al. | |
| 5,710,378 A | 1/1998 | Dykes et al. | |
| 5,781,007 A * | 7/1998 | Partika et al. | 324/220 |
| 5,826,310 A * | 10/1998 | Hobday | 24/514 |
| 6,175,234 B1 * | 1/2001 | Granger et al. | 324/219 |
| 6,339,331 B1 | 1/2002 | Ruzzo | |
| 6,426,622 B1 * | 7/2002 | Givens et al. | 324/262 |
| 6,608,478 B1 | 8/2003 | Dziech et al. | |

OTHER PUBLICATIONS

U.S. Appl. No. 10/011,190; filed Dec. 7, 2001; Dziech et al.
D.S. Sullivan et al, "M & FQT Procedure 734," Jul 22, 1992, redacted excerpts: cover, pp. 1-5 & 9-13.

* cited by examiner

*Primary Examiner*—Bot Ledynh
*Assistant Examiner*—Reena Aurora
(74) *Attorney, Agent, or Firm*—V. G. Ramaswamy; Francis L. Conte

(57) ABSTRACT

An eddy current inspection apparatus includes a holder for a specimen, a holder for an eddy current probe, and an eddy current instrument operatively joined thereto. The probe holder includes carriages for translating the probe along first and second axes. The probe holder is selectively moved to align the probe with an internal channel of the specimen for sliding movement therealong to conduct eddy current inspection thereof.

20 Claims, 3 Drawing Sheets

INTERNAL EDDY CURRENT INSPECTION

BACKGROUND OF THE INVENTION

The present invention relates generally to non-destructive testing, and, more specifically, to eddy current inspection of manufactured components.

Gas turbine engines include rotating shafts and disks which support rotating blades in the fan, compressor, high pressure turbine, and low pressure turbine. Commercial and military turbine engines used for powering aircraft in flight require minimum weight while still ensuring a suitable useful life of the engine components.

The rotating components are subject to substantial centrifugal loads during operation which generate corresponding stress that must be limited for maximizing component life. Various forms of superalloy materials are commonly used in modern aircraft turbine engines for ensuring component integrity over the useful life thereof.

However, defects, flaws, or other anomalies in the material may be introduced during the original manufacture of the engine components, or may occur during the operational life thereof. Accordingly, the engine components are typically inspected during the manufacturing process, and during routine maintenance outages, for uncovering any anomaly therein which might limit the useful life of the components.

A common, non-destructive inspection technique is eddy current (EC) inspection of typically metal components. An EC probe includes a small electrical coil mounted near the tip thereof through which an alternating current is generated, which in turn produces an eddy current in the component. The probe tip is moved along the surface of the component for inspection and is used to measure the interaction between the electromagnetic field and the component.

A defect or geometric abnormality in the material which changes the homogeneity thereof will disturb the eddy current. The disturbed eddy current modifies the exciting current in the probe coil, and the modified current is then suitably detected and correlated to particular properties of the material to indicate the corresponding anomaly.

For example, eddy current inspection is commonly used for measuring residual stress, density, and degrees of heat treatment in typically metal components. It is also typically used for detecting physical defects or abnormalities on or near the material surface such as dents, bumps, or minute cracks in the material.

Crack detection is particularly important in turbine engine components since cracks may propagate under stress and substantially reduce the useful life of a component, and may eventually lead to component failure if not suitably accommodated.

The electrical coil in a typical eddy current probe is relatively small, for example, about 0.5 mm in diameter for ensuring high sensitivity to detect very small flaws or defects in the material. Correspondingly, the small coil is very sensitive to the operating environment of the inspection equipment. For example, the probe must remain in contact with the component or specimen being inspected without any gaps therebetween which would cause false readings.

The face of the coil should be oriented substantially normal or perpendicular to the surface of the specimen for maximizing eddy current inspection performance. And, the contact pressure between the probe and the specimen should remain substantially constant as the probe slides along the specimen in order to maintain integrity of the eddy current signal and prevent lift-off of the probe from the specimen which would interrupt that signal.

Although eddy current inspection may be done manually by hand movement of the probe, automated movement of the probe is desired for ensuring accurate inspection and reducing cost for repetitive inspections of multiple features in various components. Automated eddy current inspection typically includes a holder for the specimen and another holder for the probe, with the probe being mounted for relative movement with the specimen.

The probe holder typically includes a translating carriage for permitting the operator to manually push the mounted probe for direct sliding movement against the specimen. However, the typical eddy current inspection apparatus is specifically configured for inspecting external surfaces of the specimen, with any internal cavities or channels therein typically being inspected visually using an optical borescope. Small or minute cracks in an internal channel are difficult to detect visually, and can substantially reduce the useful life of the specimen.

For example, a first stage turbine rotor blade includes a hollow airfoil fed with coolant through several inlet channels extending downwardly through the supporting dovetail thereof. The dovetail includes corresponding lobes having serpentine profiles with contact faces that transfer the substantial centrifugal loads to the supporting dovetail posts in the perimeter of the turbine rotor disk. The external surfaces of the dovetail lobes may be readily inspected using conventional eddy current equipment, yet the internal channels in the dovetail are relatively small and effectively hide the surfaces thereof from ready access.

Accordingly, it is desired to provide eddy current inspection of such internal channels in specimens with accuracy and repeatability notwithstanding the limited access thereto.

BRIEF DESCRIPTION OF THE INVENTION

An eddy current inspection apparatus includes a holder for a specimen, a holder for an eddy current probe, and an eddy current instrument operatively joined thereto. The probe holder includes carriages for translating the probe along first and second axes. The probe holder is selectively moved to align the probe with an internal channel of the specimen for sliding movement therealong to conduct eddy current inspection thereof.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
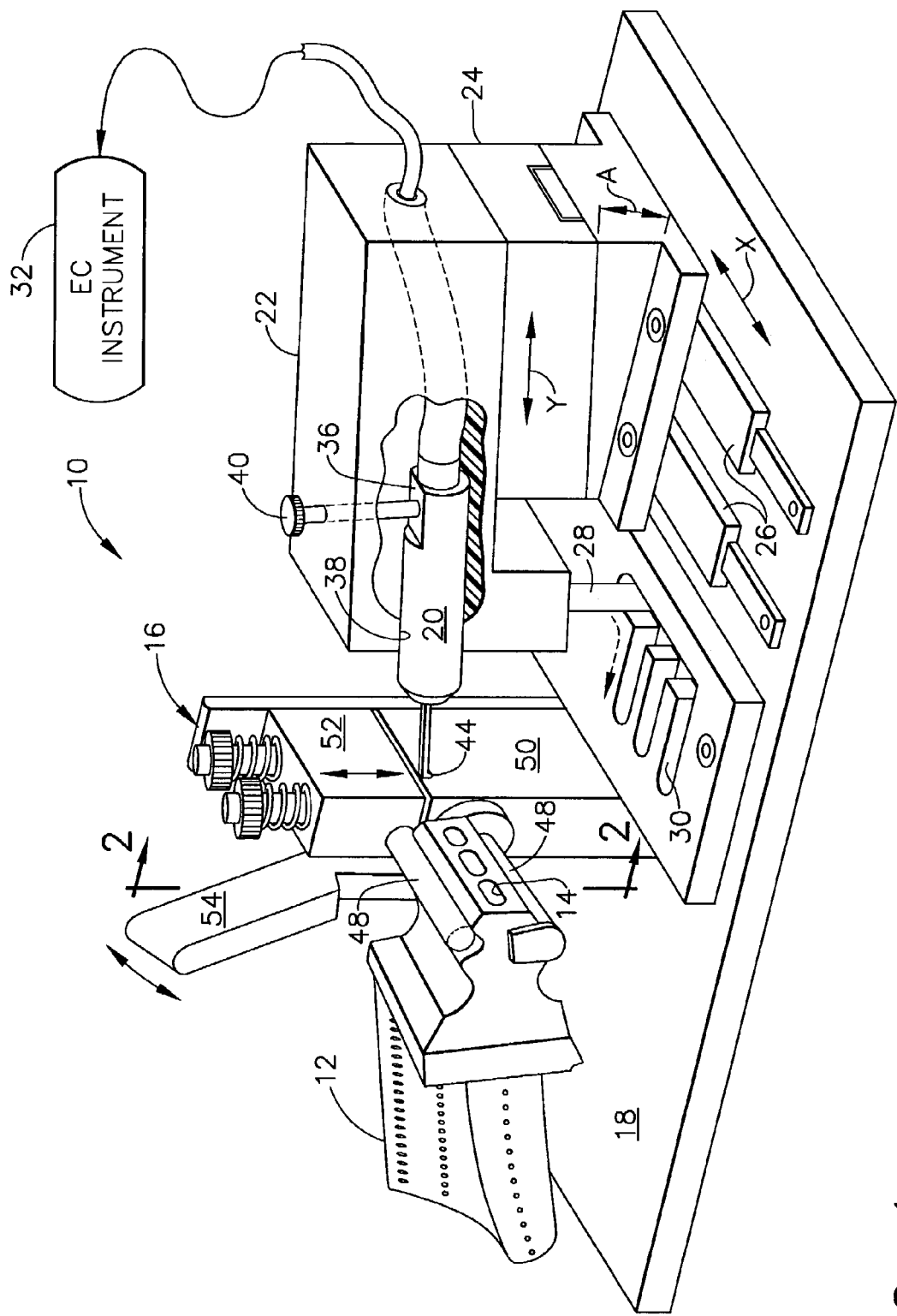
FIG. 1 is an eddy current inspection apparatus including holders for the specimen and the eddy current probe for relative movement therebetween in accordance with an exemplary embodiment.

Illustrated in FIG. 1 is an eddy current inspection apparatus 10 specifically configured for conducting eddy current inspection of a specimen 12 having one or more accessible internal passages or channels 14. The specimen may have any configuration and material composition amenable to eddy current inspection. For example, the exemplary specimen illustrated is a first stage turbine rotor blade for an aircraft gas turbofan engine.

The blade specimen 12 includes a hollow airfoil with various rows of film cooling holes for discharging coolant air therefrom during operation. The airfoil is integrally formed in a common casting with a conventional multilobed dovetail at its root end, with three exemplary internal channels 14 extending through the dovetail and into the airfoil for feeding the coolant thereto during operation.

As indicated above, turbine rotor components, such as the exemplary blade specimen, are subject to substantial centrifugal loads during operation at elevated temperature in the hot combustion gas environment of the turbine, and should be free of any defect which could substantially shorten the life thereof during operation. In one situation, turbine blades are removed from an operating engine at a periodic maintenance outage and inspected for damage or cracks which could shorten the remaining useful life thereof. The external surfaces of the blade may be inspected using any conventional technique, including, for example, eddy current inspection thereof in conventional manners.

However, the blade internal channels 14 are not amenable to conventional eddy current inspection, and are therefore typically inspected visually using an optical borescope for viewing the surfaces of the internal channels at their inlets at the bottom end of the dovetail and along their paths to the airfoil.

The inspection apparatus 10 illustrated in FIG. 1 is specifically configured for conducting eddy current inspection of any one or more of the three exemplary internal channels 14 which feed coolant through the dovetail and into the airfoil.

The apparatus includes means in the form of a specimen holder 16 for fixedly mounting the blade specimen stationary in space, such as to a common mounting stand or bed 18. An eddy current (EC) probe 20 is specifically configured to enter the limited access space of the corresponding internal channels 14 for conducting eddy current inspection thereof. Means in the form of a probe holder 22 are provided for mounting the probe in a cantilevered configuration facing the specimen channels for relative movement in respective ones thereof.

The probe holder is mounted in turn on upper and lower carriages 24,26 and supported atop the bed 18 for translating the probe 20 along orthogonal first and second axes X,Y relative to the mounted specimen 12.

The upper carriage 24 illustrated in FIG. 1 may have any conventional configuration such as a linear slide suitably mounted to the underside of the probe holder 22 for permitting sliding translation along the second axis Y. Similarly, the lower carriage 26 may be in the form of two spaced apart linear slides disposed perpendicularly or orthogonally to the upper carriage and suitably fixedly joined thereto.

In this way, the two carriages 24,26 in turn support the probe holder 22 atop the bed 18 and permit two degrees of translation along the X and Y axes generally in a common XY plane relative to the specimen 12. The specimen is preferably mounted horizontally in the specimen holder with the three exemplary channels 14 aligned in a common XY plane at a suitable elevation above the bed in general alignment with the EC probe 20.

Additional means in the exemplary form of a cooperating index pin 28 and index track 30 are provided for accurately indexing or translating the probe along the first axis X to align the probe with the specific internal channel 14 being inspected in the specimen. As shown in FIG. 1, the index pin 28 extends vertically downwardly from the forward end of the probe holder 22, and may be threaded thereto for example. Correspondingly, the index track 30 is mounted directly below the pin 28 and suitably joined to the mounting bed 18. The track is disposed adjacent to the lower carriage 26 for guiding the pin in alignment with the corresponding specimen channel 14.

In the exemplary embodiment illustrated in FIG. 1, the specimen includes three internal channels 14 which require eddy current inspection, and therefore the index track 30 includes three corresponding parallel legs or slots for receiving in turn the index pin 28. Each leg of the track is aligned parallel with the second axis Y to correspond with the orientation of the internal channels 14 mounted in the specimen holder 16 in corresponding alignment along the second axis Y. The index track is suitably located on the common bed 18 so that as the index pin 28 moves longitudinally along the corresponding leg the probe 20 is translated in alignment with the corresponding internal channel 14.

Each leg of the track 30 terminates at a forward end between the specimen and probe holders to limit the amount of insertion of the probe into the respective internal channel. Opposite back ends of the legs join together in a common transverse leg or slot which extends suitably to one side of the three legs for retracting the probe to a safely remote location away from the mounted specimen to provide suitable clearance between the probe and specimen.

Accordingly, the probe holder 22 may be manually grasped by the operator and guided by movement of the index pin from the transverse slot of the index track into each of the longitudinal legs of the track in turn which define predetermined sites therein correspondingly aligned with the respective internal channels requiring eddy current inspection.

The lower carriage 26 provides a convenient and accurate mechanism to translate the probe in its holder laterally along the X axis for direct alignment with corresponding ones of the internal channels 14 which extend along the Y axis. Correspondingly, the upper carriage 24 provides a convenient and accurate mechanism for the operator to manually feed or move the probe inside the corresponding specimen channel 14 along the second axis Y aligned with the channel. The diameter of the index pin 28 is sized to closely match the width of the corresponding legs of the index track 30 so that the probe and its holder are accurately guided toward the specimen as the pin 28 slides between the back and forward ends of the longitudinal legs during operation.

The EC probe 20 is operatively joined through a suitable electrical lead to an eddy current instrument 32 which may have any conventional configuration. By translating the mounted probe 20 into the corresponding specimen channel, eddy current inspection of the internal surfaces thereof may be conveniently, accurately, and repeatably effected as the probe slides along the surfaces thereof during eddy current inspection.

Figure 2:
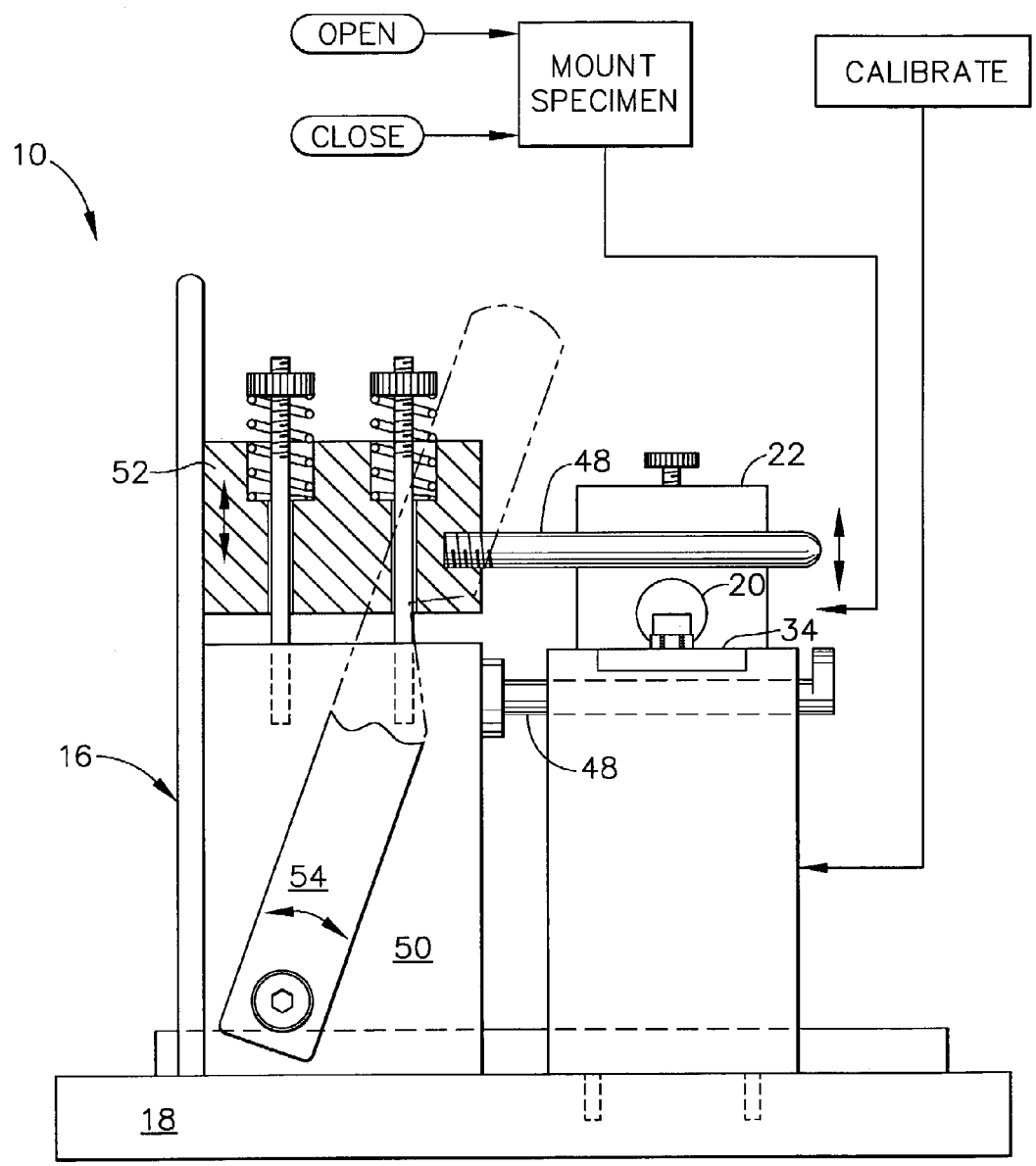
FIG. 2 is a partly sectional elevational view of the apparatus illustrated in FIG. 1 and taken along line 2—2, along with a corresponding flowchart description for calibrating the apparatus and mounting the specimen for conducting eddy current inspection.

Prior to conducting eddy current inspection, the EC probe 20 itself is typically calibrated for maximizing its sensitivity and performance during operation. FIG. 2 illustrates the initial introduction of a calibration block 34 temporarily mounted on the bed 18 using removable alignment pins extending therebetween. The calibration block 34 is an accurately machined sample of the parent material of the specimen, such as metal, in which an accurately formed minute notch is preformed by electrode discharge machining (EDM). The calibration block is mounted at a suitable elevation on the bed for engaging the probe 20 in sliding movement therewith for calibrating the specific probe in the EC instrument 32.

Figure 3:
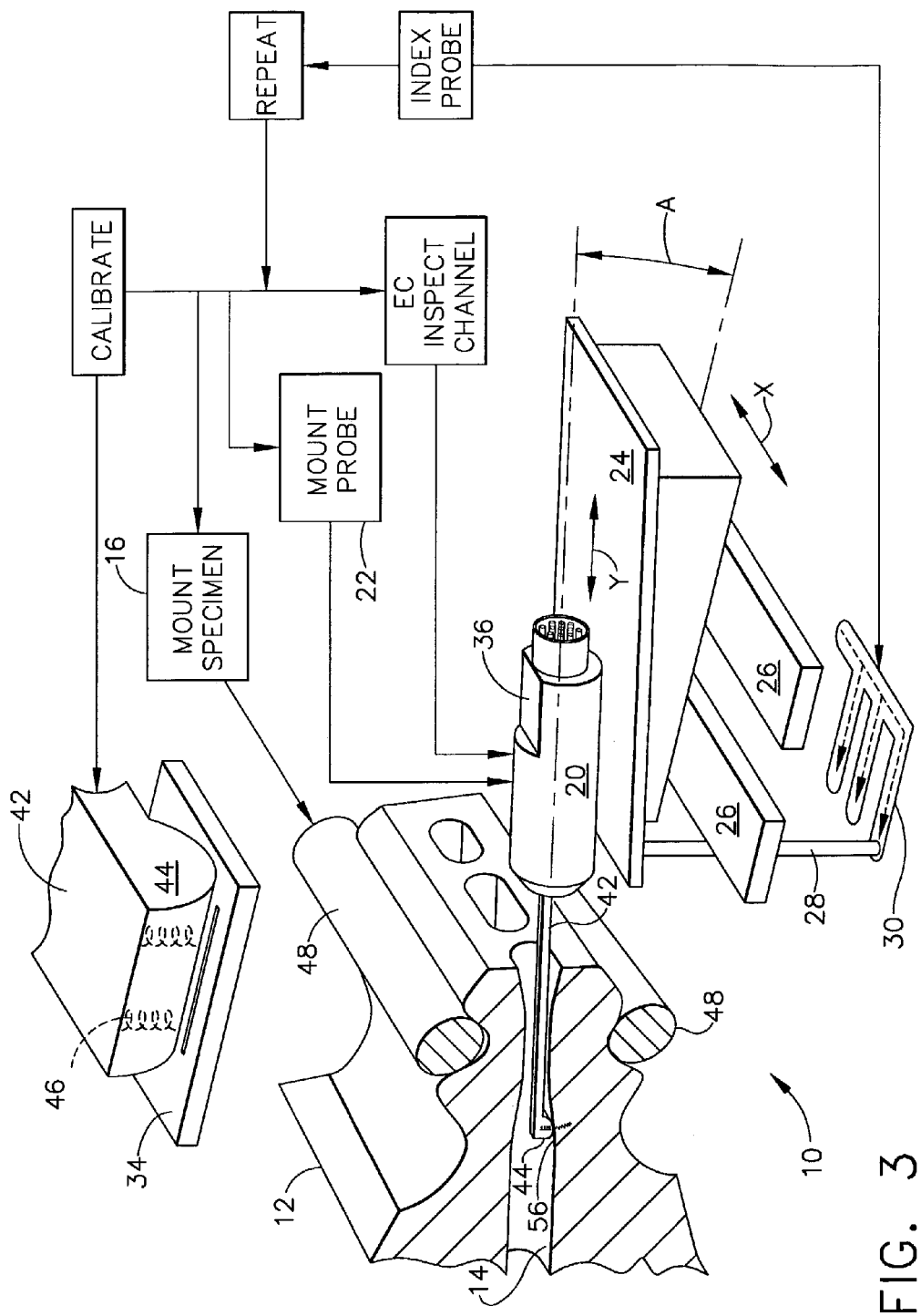
FIG. 3 is a flowchart representation of an exemplary method of calibrating the apparatus illustrated in FIGS. 1 and 2, and conducting eddy current inspection of an internal channel in the specimen.

The EC probe is illustrated schematically in a preferred embodiment in FIG. 3 and includes a generally cylindrical shank having a flat land 36. As shown in FIG. 1, the probe holder 22 includes a complementary mounting bore or collet 38 sized in diameter for receiving the probe shank in a close fit therewith. A suitable thumbscrew 40 extends through the probe holder for engagement against the shank land 36, and may be hand tightened for locking the probe in a predetermined rotary or circumferential position cantilevered from the probe holder.

The rotary position of the probe is preferably fixed since the probe itself is specifically configured to enter the correspondingly configured internal channels 14 which have generally flat opposite walls corresponding with the opposite generally concave pressure side of the blade airfoil and the generally convex suction side of the airfoil. As shown in FIG. 3, the probe also includes an elongate stem 42 cantilevered from the shank, with a probe tip 44 disposed at the distal end of the stem.

The probe tip preferably includes a pair of electrical coils 46 therein which are joined by the electrical leads to the EC instrument for conducting eddy current inspection. Each of the two coils is extremely small, with a diameter of about 1.5 mm, for ensuring sensitivity for detecting minute cracks such as the reference crack intentionally introduced in the calibration block 34 illustrated in FIG. 3, and or actual crack inside one of the internal channels 14 as also illustrated in FIG. 3.

In view of the specific configuration of the probe tip 44 and coils 46 mounted therein, the shank land 36 is provided to correspond with the desired orientation of the probe tip when fixedly mounted in probe holder 22.

As illustrated schematically in FIG. 3, the common probe 20 is mounted in the probe holder 22 and initially calibrated using the calibration block 34 temporarily mounted on the bed 18. The calibration block is then removed from the bed and the specimen 12 suitably mounted in the specimen holder 16 for conducting eddy current inspection thereof. The probe holder is then simply translated along the two carriages 24,26 to align the probe tip 44 with one of the three internal channels 14 and then sliding that probe tip 44 inside the specimen channel along the second axis Y while maintaining contact between the tip and internal surface of the channel for conducting eddy current inspection thereof.

In this way, one surface of the specimen channel may be examined using eddy current inspection over a suitable length or depth inside the entrance to the channel as permitted by the corresponding length of the probe stem 42. The probe may then be retracted from the channel by pulling the probe holder along the upper carriage 24. The probe holder is then translated laterally along the first axis X to index the probe in alignment with a second one of the internal channels in the specimen corresponding with another one of the track legs.

The probe may then be manually pushed forward on the upper carriage for sliding the probe tip 44 along the lower surface of the next internal channel undergoing eddy current inspection. In this way, each of the three exemplary internal channels 14 may be accurately examined using eddy current inspection by sliding the probe tip along the corresponding surfaces thereof as constrained by the limited movement of the upper and lower carriages along the two axes X,Y of movement, and as indexed and guided by the index pin 28 in the corresponding legs of the index track 30.

A particular advantage of the inspection apparatus 10 illustrated in the several Figures is the relative simplicity thereof for expediting eddy current inspection of multiple internal channels in the common specimen 12 with precision and repeatability, and without undesirable liftoff of the probe tip as it slides along the respective internal surface of the channel. As indicated above, the probe 20 itself is specifically configured for being accurately retained in the complementary collet 38 provided in the probe holder 22.

Correspondingly, the specimen holder 16 is specifically configured for releasably mounting the blade specimen 12 in two opposite up or down positions, with the ability to rapidly mount and remove multiple blade specimens in turn for undergoing eddy current inspection for a sequence of specimens.

More specifically, the specimen holder 16 illustrated in FIG. 2 includes a releasable bar clamp 48 for releasably mounting the specimen accurately in space and relative to the fixedly mounted EC probe. The bar clamp 48 includes a lower cylindrical clamping bar suitably mounted to a lower stand 50 which in turn is fixedly mounted to the bed 18. The bar clamp also includes a cylindrical upper clamping bar fixedly mounted to a corresponding upper stand 52.

The upper stand is resiliently mounted atop the lower stand by two vertical rods each containing a compression spring mounted in a counterbore in the top thereof for providing a clamping force for biasing the upper stand in contact atop the lower stand. The top ends of the two rods include adjustment nuts for adjusting the initial compression of the two springs, and the corresponding clamping force therefrom applied through the two clamping bars 48.

A suitable handle 54 is pivotally mounted at its proximal end to the bottom of the lower stand and is suitably mounted with a cam pin or bushing to the upper stand 52 so that lifting of the handle will in turn lift the upper stand and further compress the compression springs for separating the clamping bars and permitting mounting of the blade specimen therebetween.

As illustrated in FIG. 1, the blade specimen 12 includes a dovetail with opposite dovetail lobes having corresponding neck regions. By lifting the handle 54, the upper stand 52 and its attached clamping bar 48 are temporarily raised above the lower stand 50 and its attached clamping bar 48 to permit the dovetail lobes to be positioned between the two clamping bars. The handle 54 is then lowered to permit the opposing clamping bars 48 to engage the opposite sides of the dovetail lobes at a corresponding neck with a compression force sufficient for fixedly mounting the specimen in the holder 16.

The compression springs in the upper stand introduce sufficient clamping force in the two clamping bars to hold the specimen stationary in space for EC inspection. The lower clamping bar preferably has an L-shaped distal end and a spring-compression bearing at its proximal end between which the specimen is transversely clamped and accurately aligned with the index track.

Accordingly, the bar clamp 48 is readily opened by lifting the handle 54 so that the blade specimen 12 may be placed in the open clamp with the dovetail and internal channels 14 facing toward the probe tip 44 mounted in the probe holder.

The handle 54 is then lowered to close the clamp on the specimen and fixedly mount the specimen relative to the mounted probe. In this way, the several internal channels 14 face the probe tip 44 in generally co-linear alignment with the probe stem as controlled by the index pin 28 and track 30.

The dovetail portion of the blade specimen 12 is illustrated in an exemplary configuration in FIG. 3 and includes the three internal channels 14 having inlets at the base end of the dovetail and extending longitudinally in span through the dovetail to the airfoil. The probe is specifically mounted relative to the mounted specimen for permitting accurate alignment of the probe stem 42 and the tip 44 at the distal end thereof inside each of the channels within the reach of the length of the stem.

The exemplary configuration of each channel includes generally flat internal surfaces corresponding with the opposite pressure and suction sides of the airfoil, which internal surfaces bound the insides of the dovetail lobes, including the narrow necks between the lobes.

The exemplary internal channel 14 illustrated in FIG. 3 includes an obtuse inspection site 56 extending longitudinally along the second translation axis Y. For example, the obtuse angle may be about 168 degrees with the left innermost portion of the site being oriented substantially horizontally in space, and the right entry region of the site being inclined upwardly at about 12 degrees.

Correspondingly, the probe tip 44 illustrated in FIG. 3 is preferably arcuate or generally semi-cylindrical along the second translation axis Y, and straight laterally along the first translation axis X. The arcuate probe tip 44 includes the two coils 46 oriented therein to face downwardly toward the arcuate surface of the tip which slidingly engages the inspection site of the internal channel.

As shown in FIG. 3, the probe stem 42 is preferably coaxial with the probe shank and mounted in the probe holder 22 substantially parallel with the upper carriage 24 for parallel movement therewith. In turn, the upper carriage 24 is preferably mounted by a wedge block to the lower carriage 26 at a shallow inclination angle A, with the distal or tip end of the probe being lower in elevation than the proximal or shank end of the probe.

Accordingly, when the probe and probe holder are moved by the upper carriage 24 along the second axis Y, the probe stem 42 and its tip 44 are correspondingly moved at the same shallow inclination angle A relative to the mounted specimen channel 14.

The arcuate configuration of the probe tip 44, with the two coils 46 mounted generally vertically therein, along with the inclined mounting of the upper carriage 24 provide a corresponding inclined trajectory of movement of the probe tip along the second axis Y inside the horizontally mounted specimen channel 14. The inclined orientation of the probe tip and stem 42 positions the two coils 46 substantially normal or perpendicular to the junction of the obtuse inspection site 56. This junction is particularly significant in the blade specimen since minute cracks have been observed in this region in used turbine blades near the ends of their intended life. The specific configuration of the probe tip and shallow inclination angle thereof maximizes sensitivity of eddy current inspection in this specific obtuse inspection site 56.

Furthermore, the probe tip 44 illustrated in FIG. 3 has an extended width for permitting the use of two coils 46 laterally side-by-side for simultaneously detecting cracks along the majority of the internal surface of each channel in one pass.

The eddy current inspection process may therefore be quickly conducted for each side of the three internal channels 14 in turn by simply sliding the probe tip inside the corresponding channels along the second translation axis Y at the shallow inclination angle A to traverse the obtuse inspection site in sliding contact therewith, as well as the surfaces of the channel before and after the obtuse site. The length of the probe stem 42 is selected to permit eddy current inspection at a corresponding depth into each of the internal channels 14 within the high stress region of the mounting dovetail lobes.

Each of the three channels may be inspected by the same eddy current probe indexed from channel to channel as described above. The holder handle 54 may then be lifted for releasing the blade, which blade may then be simply turned over and remounted in the bar clamp, with the handle being released to fixedly re-mount the blade specimen. And the eddy current inspection procedure may then be repeated in each of the three internal channels for the opposite internal surfaces thereof.

The eddy current inspection apparatus disclosed above permits manual operation by a single operator of blade specimens in turn mounted in the specimen holder. Eddy current inspection may then be conducted quickly and accurately for each of the three internal channels, with precise movement of the probe tip being controlled by the index pin and cooperating index track. The cantilevered probe tip is accurately guided in sliding contact against only the intended inspection surfaces in the three channels without possibility of damage thereto by errant movement into unintended portions of the blade specimen or of the inspection apparatus itself. The probe is safely retracted after each inspection procedure suitably remote from the mounted specimen along the transverse index slot for permitting replacement of the specimen without inadvertent damage to the probe tip.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. An apparatus for eddy current inspection of an internal channel in a specimen, comprising:
   a specimen holder including a releasable bar clamp for releasably mounting said specimen;
   an eddy current probe;
   a probe holder including a collet mounting said probe in a predetermined rotary position;
   upper and lower carriages supporting said probe holder for translation along a first axis to align said probe with said specimen channel, and along a second axis to move said probe inside said channel;
   an index mechanism for indexing said probe holder along said first axis to a predetermined site aligned with said channel and constraining movement at said predetermined site on said first axis while said probe is moved along said second axis; and
   an eddy current instrument operatively joined to said probe for conducting eddy current inspection of said specimen channel.

2. An apparatus according to claim 1 wherein said upper carriage is mounted to said lower carriage at a shallow inclination angle to incline said probe at a corresponding shallow angle with said specimen channel.

3. An apparatus according to claim 2 wherein said probe comprises:
   a shank having a flat land mounted in said collet;
   a stem cantilevered from said shank and disposed at said inclination angle; and
   a tip disposed at a distal end of said stem, and including an electrical coil therein for conducting eddy current inspection.

4. An apparatus according to claim 3 wherein said bar clamp is configured to mount said specimen with said internal channel facing said probe tip in alignment with said stem.

5. An apparatus according to claim 4 wherein said index mechanism comprises:
   an index pin extending downwardly from said probe holder; and
   an index track mounted below said pin adjacent to said lower carriage for guiding said pin in alignment with said specimen channel.

6. An apparatus according to claim 5 wherein:
   said specimen includes a plurality of said internal channels facing outwardly from a common end thereof;
   said index track includes a plurality of parallel legs corresponding with said specimen channel; and
   said upper and lower carriages are configured to translate said index pin suspended from said probe holder along said legs in turn for aligning said probe with each of said specimen channels.

7. An apparatus according to claim 6 wherein:
   one of said specimen channels includes an obtuse inspection site;
   said probe tip is arcuate along said second axis and faces said coil toward said inspection site; and
   said inclination angle of said stem positions said coil substantially perpendicular to said inspection site.

8. A method for eddy current inspection of first and second internal channels in a specimen, comprising:
   fixedly mounting said specimen;
   mounting an eddy current probe for translation along first and second axes relative to said mounted specimen;
   indexing said probe along said first axis to a predetermined site to align said probe with said first channel in said specimen;
   sliding said probe inside said first channel along said second axis while constrained at said predetermined site on said first axis;
   operating said eddy current probe to inspect said first channel as said probe slides therealong:
   retracting said probe from said first channel;
   indexing said probe along said first axis to align said probe with said second channel in said specimen;
   sliding said probe inside said second channel along said second axis; and
   operating said probe to inspect said second channel as said probe slides therealong.

9. A method according to claim 8 wherein:
   said first channel includes an obtuse inspection site; and
   said probe slides inside said first channel along said second axis at a shallow inclination angle to traverse said obtuse inspection site in sliding contact therewith.

10. A method according to claim 9 wherein said probe indexing comprises:
   mounting an index pin in fixed alignment with said probe;
   fixedly mounting an index track adjacent to said pin, with said index track including a plurality of legs corresponding with said first and second channels for receiving said pin in turn; and
   moving said pin along said track legs in turn for aligning said probe with said first and second channels in corresponding turn.

11. A method for eddy current inspection of an internal channel in a specimen, comprising:
   fixedly mounting said specimen;
   mounting an eddy current probe for translation along first and second axes relative to said mounted specimen;
   indexing said probe along said first axis to a predetermined site to align said probe with said internal channel in said specimen;
   sliding said probe inside said specimen channel along said second axis while constrained at said predetermined site on said first axis; and
   operating said eddy current probe to inspect said channel as said probe slides therealong.

12. A method according to claim 11 further comprising sliding said probe inside said specimen channel along said second axis at a shallow inclination angle relative to said channel.

13. A method according to claim 11 further comprising:
   retracting said probe from said channel;
   indexing said probe along said first axis to align said probe with a second internal channel in said specimen;
   sliding said probe inside said second channel along said second axis; and
   operating said probe to inspect said second channel as said probe slides therealong.

14. A method according to claim 13 wherein said specimen mounting comprises:
   opening a clamp in a specimen holder;
   placing said specimen in said open clamp, with said specimen channel facing said probe; and
   closing said clamp on said specimen to fixedly mount said specimen relative to said probe.

15. A method according to claim 11 wherein said probe mounting comprises:
   locking said probe in a predetermined rotary position cantilevered from a probe holder;
   mounting said probe holder to an upper carriage for translation along said second axis; and
   mounting said upper carriage at a shallow inclination angle to a lower carriage for translation along said first axis.

16. A method according to claim 11 wherein said probe indexing comprises:
   mounting an index pin in fixed alignment with said probe;
   fixedly mounting an index track adjacent to said pin; and
   moving said pin along said track to a predetermined site thereon for alignment with said specimen channel.

17. A method according to claim 16 wherein said index track includes a plurality of legs for receiving said pin, with one leg corresponding with said specimen channel, and remaining legs corresponding with additional internal channels in said specimen.

18. An apparatus for eddy current inspection of an internal channel in a specimen, comprising:
   means for fixedly mounting said specimen;
   an eddy current probe;
   means for mounting said probe for translation along first and second axes relative to said mounted specimen;

means for indexing said probe along said first axis to a predetermined site to align said probe with said internal channel in said specimen;

means for sliding said probe inside said specimen channel along said second axis while constrained at said predetermined site on said first axis; and means for operating said probe to conduct eddy current inspection of said channel as said probe slides therealong.

19. An apparatus according to claim 18 wherein:

said specimen mounting means comprise a specimen holder including a releasable clamp for releasably mounting said specimen;

said probe mounting means comprise a probe holder including a collet for mounting said probe in a predetermined rotary position, and upper and lower carriages supporting said probe holder for translation along said first and second axes; and said probe operating means comprise an eddy current instrument operatively joined to said probe.

20. An apparatus according to claim 19 wherein said upper carriage is mounted to said lower carriage at a shallow inclination angle to incline said probe at a corresponding shallow angle with said specimen channel.

* * * * *